United States Patent
Skountzou et al.

(10) Patent No.: US 10,213,378 B2
(45) Date of Patent: Feb. 26, 2019

(54) SINGLE DOSE NON-ADJUVANTED CUTANEOUS TETANUS VACCINE AND USES THEREOF

(71) Applicant: Sporos Therapeutics, LLC, Bothell, WA (US)

(72) Inventors: Ioanna Skountzou, Atlanta, GA (US); E. Stein Esser, Atlanta, GA (US); Richard Compans, Atlanta, GA (US); Shaguna Seth, Bothell, WA (US)

(73) Assignee: Sporos Therapeutics, LLC, Bothell, WA (US)

( * ) Notice: Subject to any disclaimer, the term of this patent is extended or adjusted under 35 U.S.C. 154(b) by 0 days.

(21) Appl. No.: 15/066,961

(22) Filed: Mar. 10, 2016

(65) Prior Publication Data
US 2016/0263021 A1    Sep. 15, 2016

Related U.S. Application Data

(60) Provisional application No. 62/130,744, filed on Mar. 10, 2015.

(51) Int. Cl.
| | |
|---|---|
| *A61K 39/00* | (2006.01) |
| *A61K 9/00* | (2006.01) |
| *A61K 39/08* | (2006.01) |

(52) U.S. Cl.
CPC ............ *A61K 9/0021* (2013.01); *A61K 39/08* (2013.01); *A61K 2039/54* (2013.01); *A61K 2039/55* (2013.01); *A61K 2039/575* (2013.01)

(58) Field of Classification Search
CPC .................................................. A61K 9/0021
See application file for complete search history.

(56) References Cited

PUBLICATIONS

Matsuo et al (Journal of Controlled Release vol. 160 pp. 495-501) (Year: 2012).*
Seid et al (Clinical and Vaccine Immunology vol. 21 (2), pp. 253-255) (Year: 2014).*

\* cited by examiner

*Primary Examiner* — Albert M Navarro
(74) *Attorney, Agent, or Firm* — Eckman Law Group

(57) ABSTRACT

A method for preventing or treating tetanus infection in a subject, comprising administering a non-adjuvanted tetanus toxoid vaccine to the skin. The vaccine can be delivered by intradermal injection or microneedle patch and does not require cold storage.

Figure 1:
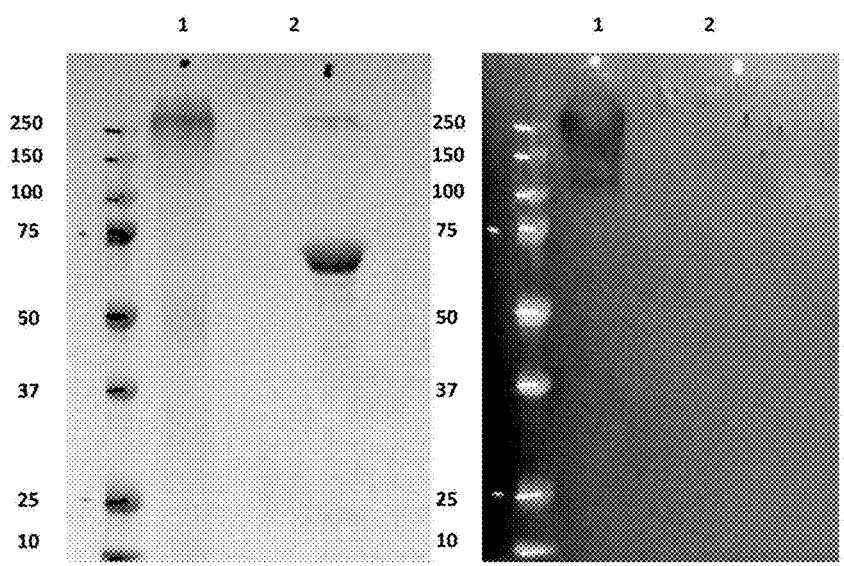

11 Claims, 19 Drawing Sheets
(18 of 19 Drawing Sheet(s) Filed in Color)

| days | MN vs ID pregnant | ID vs IM pregnant | MN vs IM pregnant | | MN vs ID non-pregnant | ID vs IM non-pregnant | MN vs IM non-pregnant |
|---|---|---|---|---|---|---|---|
| 7 | 5.9 | | | | 13 | | |
| 14 | 3 | | | | 2.3 | | |
| 28 | 2.5 | | | | 3 | | |
| 7 | | same | | | | same | |
| 14 | | 2.6 | | | | 0.65 | |
| 28 | | 2.5 | | | | 1.25 | |
| 7 | | | 6.4 | | | | 8.3 |
| 14 | | | 8.4 | | | | 1.5 |
| 28 | | | 23.6 | | | | 3.9 |

FIG. 4B

SINGLE DOSE NON-ADJUVANTED CUTANEOUS TETANUS VACCINE AND USES THEREOF

BACKGROUND OF THE INVENTION

Tetanus is an acute disease caused by a neurotoxin produced by the anaerobe *Clostridium tetani* with motor and autonomous nervous system manifestations such as rigidity and convulsive spasms. Neonatal tetanus (NT) is around 10% in these countries where antenatal care is also well below 50%. According to the latest WHO estimates in 2010, NT claimed 58,000 newborn lives and is still a major public health concern. Mothers and newborns are at high risk when delivery and umbilical cord stump are performed under unsanitary conditions leading to tissue infection. The Centers of Disease Control and Prevention (CDC) and World Health Organization (WHO) recommend vaccinations of pregnant women at 20 weeks of gestation against tetanus and other preventable diseases due to increased rate of complications in mothers and their fetuses. These immunizations not only confer protective immunity to the mother, but also provide a passive immune response to the infant prior to the development of their own antibodies. Maternal antibodies are transferred through the umbilical cord blood during fetal development and breast milk during infant nursing. Thus, two doses of tetanus toxoid can reduce mortality from neonatal tetanus by 94%.

Although tetanus is a vaccine preventable disease, it has not been fully eradicated despite the efforts of Maternal and Neonatal Tetanus (MNT) Elimination Initiative launched by UNICEF, WHO and UNFPA in 1999. The problem of inadequate vaccine coverage is more critical in developing countries where many women do not receive vaccinations before pregnancy due to limited access to health care providers. For the same reason, pregnant women deliver their babies in non-sanitary conditions resulting in high mortality rates from tetanus infections. A critical bottleneck for effective vaccination is the absence of electricity in rural areas of developing countries, which is required for vaccine transportation and storage at low temperatures.

Tetanus toxoid is a small protein with low immunogenicity, so the vaccine has low potency and requires the presence of an adjuvant (Alum) and multiple immunization doses to induce robust antibody titers and affinity maturation.

To this day tetanus infections claim at least 60,000 maternal and neonatal lives worldwide. Two doses of adjuvanted tetanus vaccine are recommended to protect pregnant women during labor and their newborns, but in many areas vaccination is still unavailable or insufficient.

It has been demonstrated that pregnancy hormones modulate maternal immunity to tolerate the developing fetus, but a downside of tolerance is the increased rate and severity of infections due to compromised immune responses. Pregnant women infected with influenza virus are at higher risk than healthy non-pregnant controls. Influenza infection-induced inflammation may compromise the well-being of their offspring by stillbirth, preterm labor, small for gestation age newborns, fetal abnormalities and even death. The Centers of Disease Control and Prevention (CDC) and World Health Organization (WHO) recommend vaccinations of pregnant women at 20 weeks of gestation against preventable diseases including tetanus, due to higher risk of complications in mothers and their fetuses. These immunizations not only confer protective immunity to the mother, but also provide a passive immune response to the infant prior to the development of their own antibodies. Maternal antibodies are transferred through the umbilical cord blood during fetal development and breast milk during infant nursing.

The problem of inadequate vaccine coverage is more critical in developing countries where many women do not receive these vaccines before pregnancy and frequently they do not have access to health care providers delivering their babies in non-sanitary conditions resulting in high mortality rates from tetanus infections. Moreover, intramuscular delivery of tetanus toxoid requires the presence of an adjuvant (Alum) due to low vaccine potency, and multiple immunization doses to induce robust antibody titers and affinity maturation.

Vaccine delivery in the skin has been shown to utilize antigen presenting cells (APCs) residing in the epidermis and the dermis, which leads to an increased immune response compared to the traditional route of intramuscular delivery. Skin vaccination during pregnancy via intradermal injection can be more immunogenic than intramuscular vaccine delivery.

What is needed are methods, compositions and devices for tetanus immunization.

There is a continuing need for methods, compositions and devices for tetanus immunization.

BRIEF SUMMARY

This invention relates to the fields of vaccines for tetanus.

More particularly, this invention relates to methods and devices for cutaneous delivery of tetanus vaccine.

Embodiments of this invention provide a single dose, non-adjuvanted tetanus toxoid vaccine that can be delivered cutaneously, either by intradermal injection, or by a microneedle patch device.

Embodiments of this invention include:

A method for preventing or treating tetanus infection in a subject, comprising administering a non-adjuvanted tetanus toxoid vaccine to the skin.

The method above, wherein the tetanus toxoid vaccine is delivered by intradermal injection or microneedle patch.

The method above, wherein the subject is pregnant.

The method above, further comprising:
administering a non-adjuvanted tetanus toxoid vaccine by placing a microneedle patch containing the vaccine on the skin of the subject;
holding the patch in place to allow the vaccine to dissolve into the skin.

The method above, wherein the microneedles of the patch penetrate the skin and the patch is held in place for at least 10 minutes.

The method above, wherein at least five-fold higher level of tetanus toxoid-specific antibodies are induced in non-pregnant subjects than for intramuscular administration in non-pregnant subjects.

The method above, wherein at least two-fold higher level of tetanus toxoid-specific antibodies are induced in pregnant subjects than for intramuscular administration in pregnant subjects.

The method above, wherein at least a six-fold higher level of tetanus toxoid-specific antibodies IgG2a are induced in a pregnant subject as compared to intramuscular administration in a non-pregnant subject.

The method above, wherein at least a ten-fold increase in antibody levels is induced at week 3 as compared to intramuscular administration.

The method above, wherein the induced ratio IgG1/IgG2a is lower as compared to intramuscular administration.

The method above, wherein the patch is loaded with commercially-available non-adjuvanted tetanus toxoid monobulk that is concentrated at least five times its original concentration.

The method above, wherein the non-adjuvanted tetanus toxoid comprises 3% polyvinyl alcohol and 10% sucrose as excipients.

A microneedle patch containing a non-adjuvanted tetanus toxoid vaccine.

The microneedle patch above, wherein the patch is loaded with commercially-available non-adjuvanted tetanus toxoid monobulk that is concentrated at least five times its original concentration.

The microneedle patch above, wherein the non-adjuvanted tetanus toxoid comprises 3% polyvinyl alcohol and 10% sucrose as excipients.

BRIEF DESCRIPTION OF THE DRAWINGS

This patent or application file contains at least one drawing executed in color. Copies of this patent or patent application publication with color drawings will be provided by the US Patent Office upon request and payment of the necessary fee.

The following drawings form part of the present specification and are included to further demonstrate certain aspects of the present disclosure, the inventions of which can be better understood by reference to one or more of these drawings in combination with the detailed description of specific embodiments presented herein.

FIG. 1 shows SDS-page analysis of tetanus toxoid. As shown in FIG. 1 (left), proteins were separated on 10% gel under denaturing conditions, transferred onto nitrocellulose membrane and reversibly stained with PONSEAU S protein stain. Tetanus toxoid (Serum Institute of India), 7.5 μg total protein. As shown in FIG. 1 (right), the same membrane developed with anti-tetanus toxoid HRP-labeled antibodies (#TTX-314, Alpha Diagnostics). Tetanus toxoid (positive control, Alpha Diagnostics kit), 7.5 μg total protein.

FIG. 2A shows an array of microneedles loaded with TT (red color to facilitate imaging).

FIG. 2B shows an array of microneedles loaded with sulforhodamine (red color to facilitate imaging).

FIG. 3A shows second-generation microneedles before insertion into mouse skin in vivo.

FIG. 3B shows second-generation microneedles 20 min after insertion into mouse skin in vivo.

FIG. 3C shows mouse skin with dissolved nicroneedles.

FIG. 4A shows Anti-TT IgG antibodies in adult non-pregnant and pregnant population.

FIG. 4B shows differences in antibody titers between pregnant, non-pregnant cohorts and routes of immunization (Table 1).

FIG. 5A shows: Anti-TT IgG antibodies.

FIG. 5B shows: Anti-TT IgG1 antibodies.

FIG. 6A shows: Survival rates in healthy adult non-pregnant population.

FIG. 6B shows: Survival rates in healthy adult population vaccinated during pregnancy.

FIG. 6C shows: Anti-TT neutralizing antibodies.

FIG. 7A shows: Survival rates of 3-week old mice after challenge with 8.33×$LD_{50}$ tetanus toxin.

FIG. 7B shows: Survival rates of 6-week old mice after challenge with 8.33×$LD_{50}$ tetanus toxin.

FIG. 8A shows evaluation of humoral responses of immunized adult mice. Serum samples from non-pregnant adult mice vaccinated either intradermally (ID) or intramuscularly (IM) were collected 7, 14, and 28 days after immunization. The samples were analyzed against tetanus toxoid for the levels of total serum IgG (FIG. 8A) antibody titers by ELISA. ELISA antibody data represent the mean±SEM. Statistics for the ID and IM group were performed with two-tailed unpaired Student's t-test. *$p<0.05$.

FIG. 8B shows evaluation of humoral responses of immunized adult mice. Serum samples from non-pregnant adult mice vaccinated either intradermally (ID) or intramuscularly (IM) were collected 7, 14, and 28 days after immunization. The samples were analyzed against tetanus toxoid for the levels of total serum IgM (FIG. 8B) antibody titers by ELISA. ELISA antibody data represent the mean±SEM. Statistics for the ID and IM group were performed with two-tailed unpaired Student's t-test. *$p<0.05$.

FIG. 9A shows protective immune response in immunized mice after lethal challenge with Tetanus Toxin. Eight week old were immunized with 5 Lf of non-adjuvanted tetanus toxoid by intradermal (ID) or intramuscular (IM) delivery. Twenty eight days later, they were challenged with 10×$LD_{50}$ tetanus toxin and observed over a 4 day period. Survival rates (FIG. 9A) during the observation period were recorded. All symptoms were categorized according to the European Pharmacopeia's scale of paralysis. T1: slight stiffness of toxin-injected hind leg, only observed when the mouse is lifted by the tail. T2: paresis of the toxin-injected hind leg, which can still function for walking. T3: paralysis of the toxin0injected hind leg, which does not function for walking. Mice displaying symptoms of stages T2 and T3 were considered unprotected and euthanized.

FIG. 9B shows protective immune response in immunized mice after lethal challenge with Tetanus Toxin. Eight week old were immunized with 5 Lf of non-adjuvanted tetanus toxoid by intradermal (ID) or intramuscular (IM) delivery. Twenty eight days later, they were challenged with 10×$LD_{50}$ tetanus toxin and observed over a 4 day period. Signs of symptoms (FIG. 9B) during the observation period were recorded. All symptoms were categorized according to the European Pharmacopeia's scale of paralysis. T1: slight stiffness of toxin-injected hind leg, only observed when the mouse is lifted by the tail. T2: paresis of the toxin-injected hind leg, which can still function for walking. T3: paralysis of the toxinOinjected hind leg, which does not function for walking. Mice displaying symptoms of stages T2 and T3 were considered unprotected and euthanized.

DETAILED DESCRIPTION OF THE INVENTION

This invention provides methods for treating tetanus infection, as well as a single dose, non-adjuvanted tetanus toxoid vaccine.

A tetanus vaccine of this disclosure can be delivered by intradermal injection, or via a microneedle patch device.

The methods and apparatus of this invention can be used for treating tetanus infection, especially in locations where cold storage is not available.

Skin immunization during pregnancy can be an alternative and efficient route to expand vaccination coverage and provide protective immunity by administering only one vaccine dose.

In this invention, host immune responses to non-adjuvanted tetanus toxoid (TT) induced by skin delivery were surprisingly greater than for conventional intramuscular immunization.

In some embodiments, skin vaccination of BALB/c mice during pregnancy via intradermal injection of non-adjuvanted tetanus toxoid vaccine, employing microneedle patches fabricated from PVA (polyvinyl alcohol) that encapsulated the non-adjuvanted vaccine, was more immunogenic than intramuscular vaccine delivery.

In certain aspects, skin vaccination via microneedle patches resulted in a greater passive immune response amongst offspring, as well as significant protective efficacy against lethal infections compared to the offspring of those vaccinated intramuscularly during pregnancy.

In further embodiments, controlled vaccine delivery with microneedle patches outperformed intramuscular or intradermal delivery of non-adjuvanted TT with hypodermic needle. Robust humoral immune responses were elicited after a single dose of 5 Lf (flocculation units) and were sufficient to fully protect the mothers and newborns against paralytic disease or death after lethal challenge with tetanus toxin.

In further aspects, induction of TT-specific IgG titers with microneedle patches was surprisingly higher than systemic vaccination. This showed that the invention can improve affinity maturation following isotype class switching. Protective immunity can be a reliable parameter to compare the efficacy of vaccination platforms.

In some embodiments, two types of effector CD4+ T helper cell responses can be induced by professional antigen presenting cells, designated Th1 and Th2, each designed to eliminate different types of pathogens. Although Th1 responses are more effective against intracellular pathogens and viruses due to cell mediated immunity triggered by IFN-γ production and subsequent activation of macrophages and B cell-secreted opsonizing and complement fixation antibodies, Th2 responses are significant for humoral immunity necessary for bacterial pathogens including tetanus due to neutralizing antibody production by IL-4-activated B cells.

In some embodiments, skin immunization with microneedle patches can induce both humoral and cellular immune responses. Thus, skin immunization is a surprisingly effective vaccine delivery platform in conferring protective immunity against lethal challenge with tetanus toxin.

Embodiments of this invention can also provide a protocol for tetanus toxin challenge in mice and establish an $LD_{50}$.

This invention encompasses novel microneedle patches for skin immunization to improve immunity of pregnant mothers against tetanus infections and increase protection of offspring early after birth. Skin can be a desirable vaccine target organ because it has an increased number of professional antigen presenting cells (APCs). Microneedles or micron-scale needles can be used to administer vaccines, therapeutics, and other materials into cells and tissues, including the skin. The vaccine can be targeted to antigen-presenting cells in the skin, allowing administration of lower doses and generating more potent, longer-lasting immune responses. Microneedle patches of this disclosure can be bio-degradable, and not leave any bio-hazardous sharps after administration. Microneedle patches of this disclosure can provide vaccine stability and storage at ambient temperatures, to facilitate self-administration and expanded geographical vaccination coverage.

In general, the skin is composed of three superimposed layers: the epidermis, the dermis and the subcutaneous tissue. The skin layers contain large numbers of specialized antigen presenting cells (APCs), which can be targets for vaccine delivery. The epidermis is rich in innate cell populations, namely keratinocytes, melanocytes, Langerhans cells expressing $CD207^+$ $CD1a^+$ in humans, and $CD207^+$ $CD205^+$ $CD11c^+$ $Cd11b^+$ in mice. The dermis is rich in Langerin positive ($CD207^+$ $CD11c^+$ $CD11b^{low}$ $CD205^-$ $CD^{103+}$) and Langerin negative ($CD207^-$ $CD11c^+CD11b^+$ $CD205^+$) dermal dendritic cells (dDCs), macrophages and mast cells. Langerhans cells and dermal dendritic cells are characterized by differential chemokine receptor expression and cytokine production.

In this invention, cutaneous immunization can be used to provide antigen capture and processing by APCs, which can be activated to migrate towards the proximal lymph nodes. Cutaneous immunization can be achieved by intradermal injection of a tetanus vaccine of this invention, or though the use of a microneedle patch of this invention.

In general, migration of APCs depends on the cutaneous environment, and the balance between pro- and anti-inflammatory signals. The presentation of processed antigen to immature CD4 or CD8 T cells or naïve follicular B cells can result in clonal expansion of T cells to effector and memory populations or activation of B cells to plasma cells or plasmablasts.

Embodiments of this invention can provide surprisingly increased effectiveness of tetanus vaccine, as compared to systemic immunization delivered to the muscle.

Example 1

Vaccines. Non-adjuvanted tetanus toxoid was provided by the Serum Institute of India. Commercially available alum-adjuvanted tetanus toxoid vaccine was purchased from IBSS Biomed S.A. (Krakow, Poland). Vaccine stability was tested with ELISA (Alpha Diagnostics International Inc., San Antonio, Tex.) and SDS-page analysis of tetanus toxoid. Tetanus toxoid and positive control were separated on 10% gel under denaturing conditions, transferred onto nitrocellulose membrane which was either reversibly stained with PONSEAU S protein stain or developed with anti-tetanus toxoid HRP-labeled antibodies (Alpha Diagnostics).

Animals. Six to 8-week-old female BALB/c mice (Harlan Laboratories, Dublin, Va.) were bred and housed in a biosafety level 1 facility for immunizations, and tetanus challenges were performed in a biosafety level 2 facility (Emory University Whitehead animal facility).

Determination of lethal dose 50 ($LD_{50}$) in BALB/c mice. Healthy adult BALB/c mice 6-weeks old were divided in groups of five and challenged with tetanus toxin (Sigma-Aldrich, St. Louis, Mo.) at concentrations of 100, 50, 10, 5, 2, 1, and 0.1 ng/50 ul PBS via subcutaneous injection in the dorsal surface of their right hind leg. The mice were examined twice a day, once in the morning and once in the evening for four days post-challenge. The experiment was repeated twice. The effect of tetanus toxin on mice was measured based on European Pharmacopeia's scale of paralysis and symptoms were recorded twice per day up to 4 days. The stages of tetanus are: T0=Normal; T1=Slight Stiffness of toxin injected hind leg, only observed when mouse is lifted by the tail; T2=paresis of the toxin injected hind leg, which can still function for walking; T3=paralysis of the toxin-injected hind leg, which does not function for walking; T4=the toxin-injected hind leg is completely paralyzed.

Adult immunizations, lethal challenge and sample collection. Groups of ten pregnant or non-pregnant mice received a single dose of non-adjuvanted tetanus toxoid containing 5 Lf for intramuscular (IM), intradermal (ID) and microneedle (MN) immunization. Pregnant mice were vaccinated on day 12 of gestation. For cutaneous immunization, the dorsal hair was removed. Dissolving microneedle patches encapsulating the antigen were placed on the skin, and held in place for 20 minutes to allow the vaccine to dissolve in the skin. For intramuscular vaccinations, the non-adjuvanted TT was diluted in 50 μl of PBS and injected into the upper quadrant of the hind leg.

Blood samples were collected from adult pregnant and non-pregnant mice via submandibular bleeds at days 7, 14, and 28 post-immunization. The offspring of pregnant mice were bled at weeks 3, 4, 5, 6, 8, 10, and 12 from birth to assess humoral responses. Following blood collection, the serum was separated via centrifugation and stored at −20° C.

At day 35 post-immunization, adult immunized mice were challenged with $50 \times LD_{50}$ of tetanus toxin (Sigma-Aldrich, St. Louis, Mo.) administered subcutaneously in the dorsal surface of their right hind leg. Disease progression was monitored twice daily for signs of paralysis (stage T1-T4), morbidity (decreased mobility, and weight loss) and mortality for 4 days. Their protective immunity was compared to unimmunized naïve mice.

A separate cohort of 3 week-old pups were challenged with $8.33 \times LD_{50}$ of tetanus toxin and observed for signs of paralysis for 4 days. All mice were humanely euthanized within 24 hours after exhibiting either paresis of the hind leg while still maintaining the ability to walk (stage T2) or paralysis of the hind leg and lacked the ability to function (stage T3). Their protective immunity was compared to unimmunized naïve mice.

All mice were euthanized according to IACUC guidelines when they reached one of the following endpoints: Paralysis of the hind leg in accordance with stage T3 in European Pharmacopeia's scale of paralysis or weight loss exceeding 25% of the starting body weight.

Evaluation of humoral immune responses. Anti-tetanus toxoid specific antibody levels were determined quantitatively by ELISA according to the manufacturer's instructions; the plates were coated with tetanus toxoid (Enzo Life Sciences, Inc., Farmingdale, N.Y.) diluted in PBS, 100 ng total protein per well. Neutralizing antibody titers were determined using an in vivo tetanus toxin neutralization assay. For each group, equal amounts of sera taken from all animals were pooled and serially diluted in PBS. An equal volume of tetanus toxin (dosages: $5 \times LD_{50}$ for adults and $2 \times LD_{50}$ for young) was mixed with the serum dilutions and incubated overnight at +4° C. The following day, each mixture was subcutaneously injected into a single naïve mouse and survival was monitored over a 4 day period. Titers were established as the inverse serum dilutions that demonstrated protection.

Fabrication of dissolving microneedle patches for encapsulation of tetanus toxoid vaccine. PDMS molds were fabricated (GA Tech laboratory) and were used to prepare microneedle patches (MN) carrying tetanus toxoid (TT). 10×10 parallel rows of conical microcavities were etched by precisely focused laser. Each individual cavity was 650 μm deep and 250 μm at base diameter.

Since the total volume of all those cavities was approximately 1.6 μL, the original non-adjuvanted tetanus toxoid monobulk obtained from the manufacturer (Serum Institute of India) was concentrated 5 and 10 times its original concentration by ultrafiltration using 10 kDa MWCO spin filters (EMD Millipore, Billerica, Mass.). The TT solution was modified by addition of 3% polyvinyl alcohol (PVA) (Sigma-Aldrich St Louis, Mo.) and 10% sucrose (Sigma-Aldrich) as excipients to increase protein stability and improve geometrical shape of the microneedle. A 5 μL mixture of the vaccine and additives was loaded to fill in the cavities and stay on a mold's surface. Vacuum was applied to force the TT mixture to fill into the mold's cavities and excess of solution was wiped off. The casting solution was air-dried in the cavities. Twenty-four hours later, a second solution of 20% PVA and 20% sucrose was loaded onto the mold to fill the remaining free space in the cavities and the mold's surface. Vacuum was applied followed by air-drying in order to form a hard backing. The resulting microneedles had a conical shape with 650×250 μm dimension, and TT was localized at the tip of the microneedles. Strength of microneedles was checked before and after short-term skin insertion under the microscope, and were not bent or brittle.

Statistics. For ELISAs, the statistical significance of differences between two groups was calculated by two-tailed unpaired Student's t-test. For survival curves, statistics were calculated using a Log-rank (Mantel-Cox) test. A p value less than 0.05 was considered significant (on graphs: * $p<0.05$;  $p<0.01$; * $p<0.001$).

Example 2

Vaccine stability. We found that more than 95% TT was retained above the membrane suggesting that the tetanus toxoid preparation was intact and therefore suitable for microneedle fabrication (data not shown). The intact structure of TT was further shown by electrophoresis and Western blot (FIG. 1). FIG. 1 shows three oligomeric components of tetanus toxoid protein, ranging from a monomer of 150 kDa to a dimer of 270 kDa. Freezing/thawing and maintaining TT at room temperature for several days had little effect on vaccine stability, as determined by ELISA.

Example 3

Figure 2A:
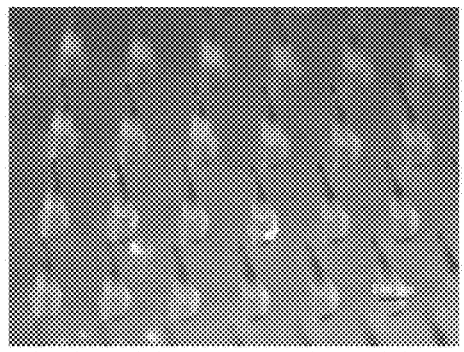
Figure 2B:
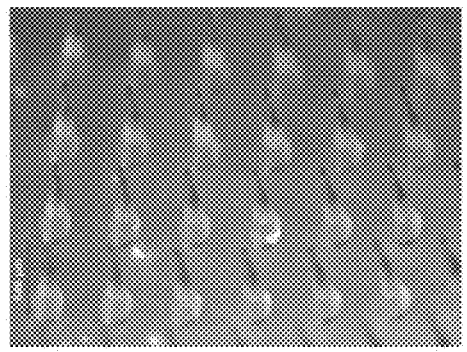

Microneedle fabrication. The microneedles penetrated the skin. To decrease dose variability due to variable insertion depth into the skin, the TT loading solution was concentrated at the microneedle tip. To assess insertion efficacy, sulforhodamine B was added to the solution to facilitate imaging of the microneedles (FIG. 2A and FIG. 2B).

Example 4

Stability of TT was tested with ELISA before and after concentration. Microneedle patches encapsulating TT were dissolved in ELISA buffer for quantitation of the antigen (Lf units per patch). Tetanus toxoid patches containing unconcentrated antigen had 0.6±0.075 Lf per patch. Patches with 10× concentrated TT had 5.5±0.7 Lf each, which was close to the required dose for human vaccines (5 Lf) delivered intramuscularly.

Figure 3A:
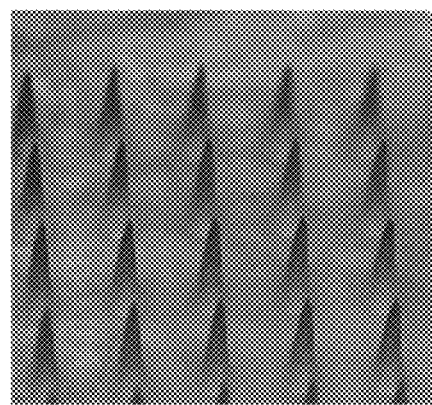
Figure 3B:
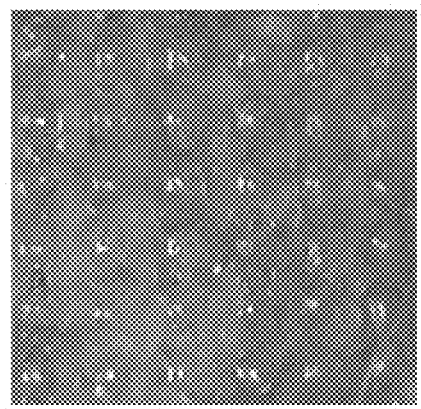
Figure 3C:
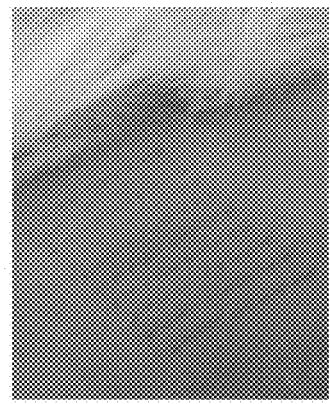

The formulation of TT microneedle patches described above led to successful penetration of murine skin, and dissolving after 20 min (FIG. 3A, FIG. 3B, and FIG. 3C). The data demonstrated that rigid TT patches can penetrate skin.

Example 5

Figure 4A:
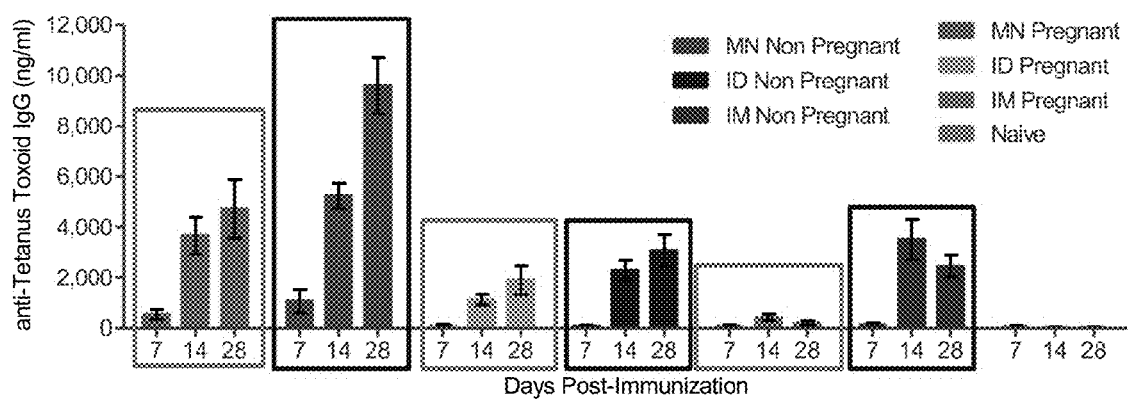

Humoral immune responses in mothers. A single dose of intramuscular delivery of non-adjuvanted TT in pregnant mice induced very low TT-specific antibodies, being the least effective vaccination approach (FIG. 4A).

In contrast, intradermal vaccination surprisingly increased the humoral responses in pregnancy as early as 14 days, reaching 2.5-fold higher titers than for intramuscular vaccination up to last bleed, and as early as day 7 for microneedle patch vaccination with titers rising from 6-fold to 23-fold (p<0.00) on day 28 post-vaccination when compared to intramuscular vaccination.

Further, although pregnant mice produced overall higher antibody titers against TT than non-pregnant mice, skin immunization-induced antibody production showed the same fold-differences over intramuscular vaccination between pregnant and non-pregnant animals in second (day 14) and third bleed (day 28).

In contrast, for the ID vs. IM induced titers in pregnant and non-pregnant animals, the differences surprisingly improved two-fold in pregnancy. This effect was even more pronounced in mice immunized with microneedle patches with 6-fold higher MN vs. ID ratios between pregnant and non-pregnant populations (FIG. 4B, Table 1). Without wishing to be bound by any particular theory, the skin may be under regulatory control of pregnancy hormones.

Example 6

Figure 5A:
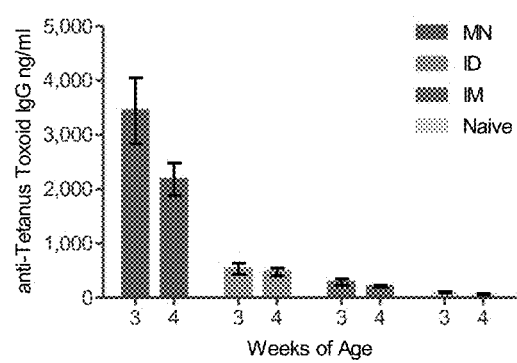
Figure 5B:
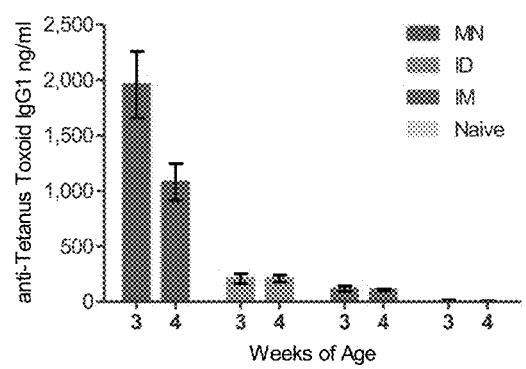

Passive immune response in offspring of vaccinated mothers. Serum samples were collected from offspring of mothers vaccinated during pregnancy at various time points following weaning at 3 weeks-old. The samples were analyzed for the levels of serum anti-TT IgG antibodies. While the titers gradually decreased in both groups over time, there was a surprising 10-fold difference in antibody levels between the MN and IM groups by week 3 (p<0.001) and a 5-fold difference between MN and ID groups (p<0.001) indicating a greater passive immune response as a result of microneedle vaccination (FIG. 5A). Similar differences were observed in IgG1 isotypes reflecting a Th2 immune profile (FIG. 5B).

In contrast to MN vaccination that produced IgG2a antibodies, none of the other vaccine delivery approaches elicited any significant IgG2a responses. As a result, the IgG1/IgG2a ratio which indicates a Th1 or a Th2 bias varied from very low in MN immunization (IgG1/IgG2a=23), suggesting activation of both arms of immunity, to very high in ID immunization, suggesting a preponderance of Th2 responses, which is more effective against toxins (IgG1/IgG2a=200).

Example 7

Figure 6A:
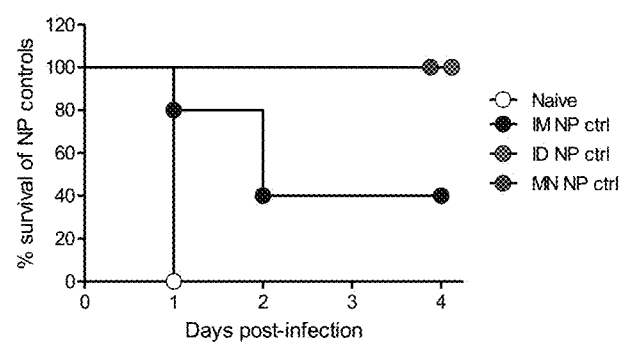
Figure 6B:
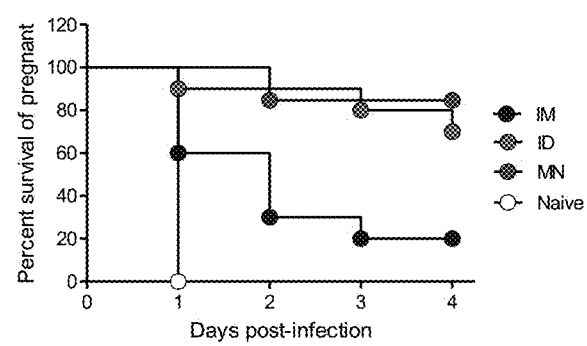
Figure 6C:
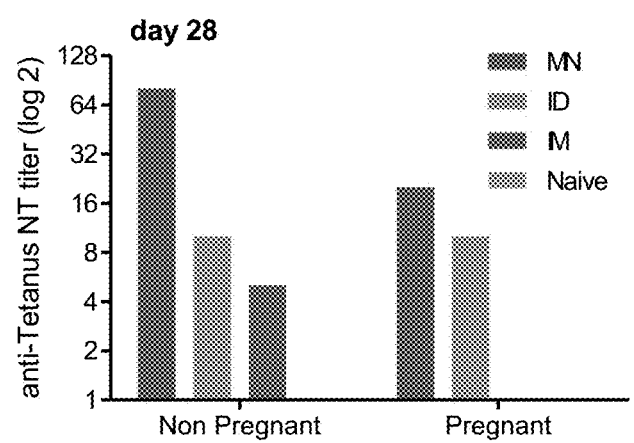

Protective immunity of vaccinated mice against lethal dose of tetanus toxin. Twenty-eight days after immunization, adult mice vaccinated were challenged with $50 \times LD_{50}$ tetanus toxin and monitored for stages T1-T3 of paralysis for 4 days. Mice showing stage T2-T3 were euthanized according to IACUC protocol. A 100% survival rate was observed in both MN and ID vaccinated mice whereas the IM immunized group survived by 40% (FIG. 6A). Similar effect of MN and ID immunization was observed in mice that received TT vaccination during pregnancy. An 84% survival rate was observed in mice immunized with microneedles, 70% survival rate in intradermally immunized mice while a 20% survival rate was observed in mice that were immunized intramuscularly (FIG. 6B). Anti-tetanus NT titer is shown in FIG. 6C.

The results show that skin antigen delivery surprisingly outperformed intramuscular immunization, despite the different effects they exerted in antibody or cell mediated immunity.

The results show that intramuscular immunization conferred 50% lower protection in pregnant animals than non-pregnant controls, whereas skin immunization-induced survival was only 15-30% lower in pregnant population when compared to non-pregnant cohort.

Figure 7A:
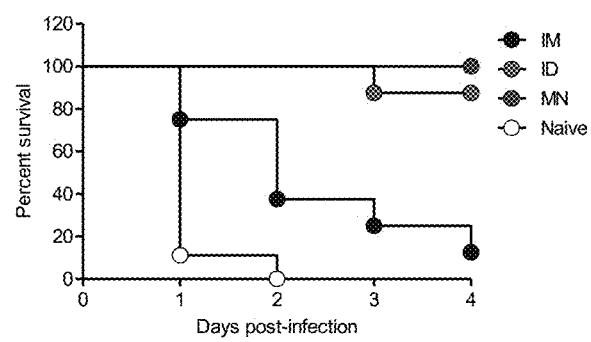

Potency of transplacentally transferred maternal anti-TT IgG antibodies to their fetuses was tested in 3 week old pups after challenge with $8 \times LD_{50}$ of tetanus toxin subcutaneously injected and observed for stages T1-T3 of paralysis for 4 days. A 13% survival rate was observed in pups born to pregnant mice immunized intramuscularly with 5 Lf Tetanus Toxoid, whereas a 100% survival rate was observed in pups born to mice immunized with the same dose using microneedles and 87.5% to offspring born to mice intradermally immunized (FIG. 7A).

Figure 7B:
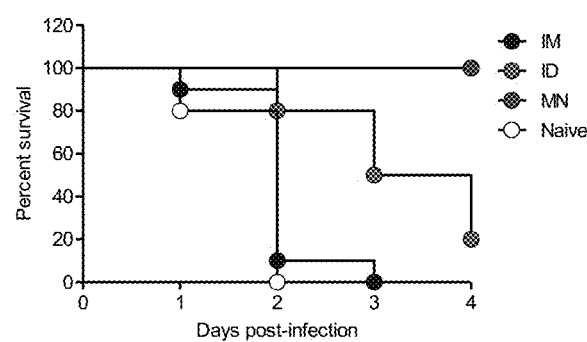

The results of this protection study demonstrate surprisingly increased potency and effectiveness due to passive immunity elicited by skin immunization, as compared to conventional antigen delivery. Six week old pups from microneedle immunized mice were fully protected, as compared to the ID group and IM groups that survived 20% and 0%, respectively (FIG. 7B). The results demonstrated surprising longevity of passive immunity elicited by skin immunization with microneedle patches.

Example 8

This study demonstrated improved protective immunity in healthy adult female mice. For the second experiment, adult female mice (8 weeks old) were immunized once with 5 Lf units of non-adjuvanted tetanus toxoid (Research Institute of India) either intradermally or intramuscularly and sera were collected on days 7, 14 and 28 post-vaccination.

Figure 8A:
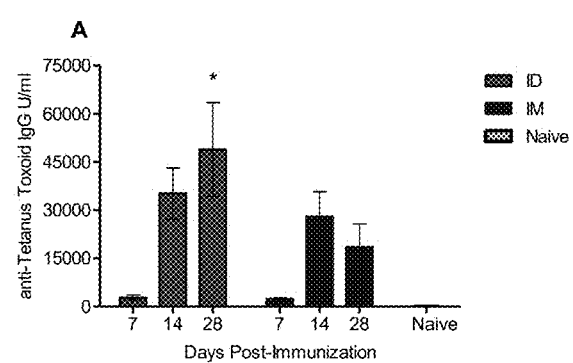
Figure 8B:
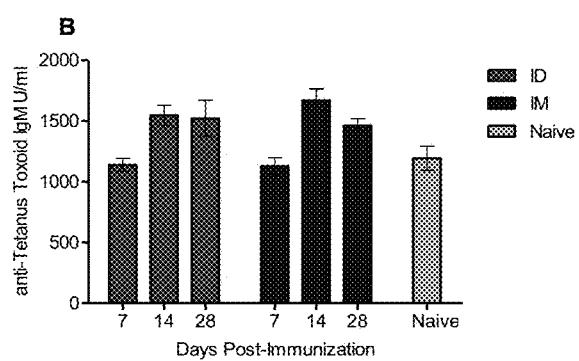

The humoral immune responses of each treatment group were IgG and IgM binding antibody titers were assessed with mouse anti-tetanus toxin/toxoid ELISA kits (Alpha Diagnostic International, San Antonio, Tex.). For total IgG (FIG. 8A), both vaccinated groups exhibited significant increases in antibody titers after 14 days compared to the nearly undetectable naïve controls. However, after 28 days, skin immunized (ID) mice continued to increase while IM immunized mice decreased resulting in an over 2-fold difference in IgG antibody titers between the groups (p<0.05). For IgM antibody titers both groups showed slight increases in IgM production (FIG. 8B), but remained statistically insignificant from the naïve controls after 28 days.

Figure 9A:
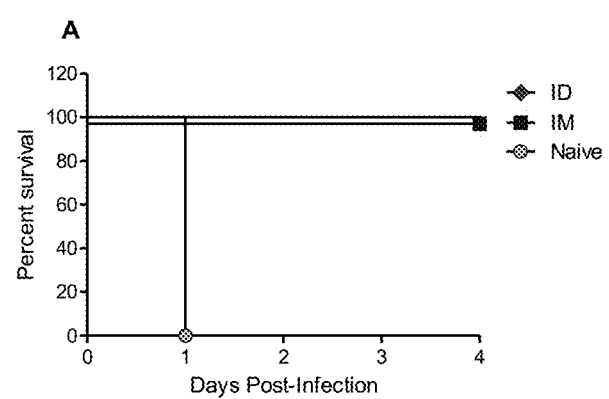
Figure 9B:
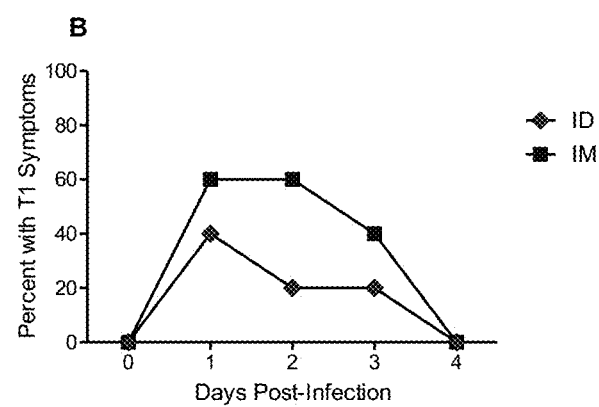

At 28 days post-immunization, the vaccinated groups and naïve (unvaccinated) controls were infected with $10 \times LD_{50}$ tetanus toxin (Sigma-Aldrich, St. Louis, Mo.) by subcutaneous injection in the hind-leg and monitored for four days in order to assess the protective immune response after lethal challenge. Mice were characterized based on European Pharmacopeia's scale of paralysis and symptoms were recorded each day. All naïve controls were euthanized within 24 hours after exhibiting either paresis of the hind leg while still maintaining the ability to walk (stage T2) or paralysis of the hind leg and lacked the ability to function (stage T3). There was a 100% survival rate for both vaccinated groups during the challenge period (FIG. 9A). However, mice from both groups (60% IM, 40% ID) appeared to have slight stiffness of the toxin-injected hind leg symptomatic of the T1 stage before fully recovering (FIG. 9B).

Skin immunization during pregnancy is a novel approach to boost the immune response in both mother and fetus. Tetanus toxoid skin immunizations in adult mice demonstrated a significant increase in IgG antibody titers compared to routinely applied intramuscular injection without the use of alum adjuvant or a secondary booster shot and more likely result in increased passive transfer during pregnancy and nursing.

All publications and patents and literature specifically mentioned herein are incorporated by reference for all purposes.

It is understood that this invention is not limited to the particular methodology, protocols, materials, and reagents described, as these may vary. It is also to be understood that the terminology used herein is for the purpose of describing particular embodiments only, and is not intended to limit the scope of the present invention, which will be encompassed by the appended claims.

It must be noted that as used herein and in the appended claims, the singular forms “a”, “an”, and “the” include plural reference unless the context clearly dictates otherwise. As well, the terms “a” (or “an”), “one or more” and “at least one” can be used interchangeably herein. It is also to be noted that the terms “comprises,” “comprising”, “containing,” “including”, and “having” can be used interchangeably.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose.

What is claimed is:

1. A method for preventing or treating tetanus infection in a pregnant subject, comprising administering a non-adjuvanted tetanus toxoid vaccine to the skin of the subject; wherein the non-adjuvanted tetanus toxoid vaccine comprises 3% polyvinyl alcohol and 10% sucrose as excipients.

2. The method of claim 1, wherein the vaccine does not require cold storage or cold transport.

3. The method of claim 1, wherein the tetanus toxoid vaccine is delivered by intradermal injection or microneedle patch.

4. The method of claim 1, further comprising:

administering a non-adjuvanted tetanus toxoid vaccine by placing a microneedle patch containing the vaccine on the skin of the subject;

holding the patch in place to allow the vaccine to dissolve into the skin.

5. The method of claim 4, wherein the microneedles of the patch penetrate the skin and the patch is held in place for at least 10 minutes.

6. The method of claim 4, wherein at least five-fold higher level of tetanus toxoid-specific antibodies are induced in non-pregnant subjects than for intramuscular administration in non-pregnant subjects.

7. The method of claim 4, wherein at least two-fold higher level of tetanus toxoid-specific antibodies are induced in pregnant subjects than for intramuscular administration in pregnant subjects.

8. The method of claim 4, wherein at least a six-fold higher level of tetanus toxoid-specific antibodies IgG2a are induced in a pregnant subject as compared to intramuscular administration in a non-pregnant subject.

9. The method of claim 4, wherein at least a ten-fold increase in antibody levels is induced at week 3 as compared to intramuscular administration.

10. The method of claim 4, wherein the induced ratio IgG1/IgG2a is lower as compared to intramuscular administration.

11. The method of claim 4, wherein the patch is loaded with commercially-available non-adjuvanted tetanus toxoid monobulk that is concentrated at least five times its original concentration.

* * * * *